(12) United States Patent
Robinson et al.

(10) Patent No.: US 9,632,409 B2
(45) Date of Patent: Apr. 25, 2017

(54) FULLERENES

(71) Applicants: Alex Phillip Graham Robinson, Birmingham (GB); Richard Edward Palmer, Southbridge (GB); Andreas Frommhold, Gera (DE); Dongxu Yang, Birmingham (GB)

(72) Inventors: Alex Phillip Graham Robinson, Birmingham (GB); Richard Edward Palmer, Southbridge (GB); Andreas Frommhold, Gera (DE); Dongxu Yang, Birmingham (GB)

(73) Assignee: Irresistible Materials LTD, Chelhydra Walk, Maritime Quarter, Swansea, Wales (GB)

( * ) Notice: Subject to any disclaimer, the term of this patent is extended or adjusted under 35 U.S.C. 154(b) by 0 days.

(21) Appl. No.: 14/899,278

(22) PCT Filed: May 21, 2014

(86) PCT No.: PCT/US2014/038997
§ 371 (c)(1),
(2) Date: Dec. 18, 2015

(87) PCT Pub. No.: WO2014/190070
PCT Pub. Date: Nov. 27, 2014

(65) Prior Publication Data
US 2016/0139506 A1    May 19, 2016

Related U.S. Application Data

(60) Provisional application No. 61/826,342, filed on May 22, 2013.

(51) Int. Cl.
*G03F 7/027* (2006.01)
*G03F 7/004* (2006.01)
(Continued)

(52) U.S. Cl.
CPC .......... *G03F 7/0042* (2013.01); *C07C 69/753* (2013.01); *C07C 69/96* (2013.01);
(Continued)

(58) Field of Classification Search
CPC ......... G03F 7/027; G03F 7/038; C07C 69/96; C07C 69/753; C07C 2104/00; H01L 51/0047
(Continued)

(56) References Cited

U.S. PATENT DOCUMENTS 6,117,617 A * 9/2000 Kanayama ............... G03F 7/038
430/296
8,815,124 B2 * 8/2014 Laird .................... B82Y 10/00
136/244

(Continued)

FOREIGN PATENT DOCUMENTS

JP    2006265130 A  * 10/2006
JP    2009161510 A  *  7/2009
JP    2013180980 A  *  9/2013

OTHER PUBLICATIONS

Clifford et al, "Photoinduced Electron and Energy Transfer Processes in Fullerene C60-Metal Complex Hybrid Assemblies", Comptes Rendus Chimie 9 (2006) p. 1005-1013.*
(Continued)

*Primary Examiner* — Amanda C Walke
(74) *Attorney, Agent, or Firm* — The Patent Practice of Szmanda & Shelnut LLC; James G. Shelnut; Charles R. Szmanda (57) ABSTRACT

The present disclosure relates to novel fullerene derivatives, positive and negative photoresist compositions prepared therefrom and methods of using them. The derivatives, their photoresist compositions and the methods are ideal for high speed, fine pattern processing using, for example, ultraviolet
(Continued)

Pitch 44nm (22nm lines): 31.2 mJ/cm² radiation, extreme ultraviolet radiation, beyond extreme ultraviolet radiation, X-rays, electron beam and other charged particle rays.

19 Claims, 5 Drawing Sheets

(51) Int. Cl.
    *C07C 69/753* (2006.01)
    *C07C 69/96* (2006.01)
    *H01L 51/00* (2006.01)
    *G03F 7/038* (2006.01)
    *G03F 7/039* (2006.01)
    *C07D 401/14* (2006.01)
    *C07D 401/04* (2006.01)

(52) U.S. Cl.
    CPC ......... *C07D 401/04* (2013.01); *C07D 401/14* (2013.01); *G03F 7/0043* (2013.01); *G03F 7/0045* (2013.01); *G03F 7/0046* (2013.01); *G03F 7/027* (2013.01); *G03F 7/0382* (2013.01); *G03F 7/0392* (2013.01); *H01L 51/0047* (2013.01); *C07C 2104/00* (2013.01)

(58) Field of Classification Search
    USPC .......................... 430/270.1, 285.1; 558/275
    See application file for complete search history.

(56) References Cited

U.S. PATENT DOCUMENTS 9,166,171 B2 * 10/2015 Ohno ..................... B82Y 10/00
9,256,126 B2 * 2/2016 Robinson ................ G03F 7/027
2005/0255332 A1 * 11/2005 Katz ..................... B01J 20/3204
                                                                     428/524
2009/0101200 A1 * 4/2009 Nakamura ............. B82Y 10/00
                                                                     136/252
2010/0035181 A1 * 2/2010 Sakaguchi .............. G03F 7/091
                                                                    430/271.1
2010/0065123 A1 * 3/2010 Gust, Jr. ................ B82Y 10/00
                                                                    136/263
2010/0081082 A1 * 4/2010 Yoshimura ................ G03F 7/11
                                                                    430/270.1
2010/0317767 A1 * 12/2010 Tanaka ................... B82Y 10/00
                                                                    523/400
2011/0177459 A1 * 7/2011 Ogihara ................ B82Y 10/00
                                                                    430/323
2012/0030926 A1 * 2/2012 Toh .......................... B21J 15/14
                                                                  29/525.03
2012/0251953 A1 * 10/2012 Robinson ............... B82Y 30/00
                                                                  430/285.1
2013/0035394 A1 * 2/2013 Mayo ..................... A61K 31/015
                                                                  514/616
2013/0074920 A1 * 3/2013 Echegoyen ......... H01L 51/0035
                                                                    136/256
2013/0202999 A1 * 8/2013 Iwato ....................... G03F 7/004
                                                                  430/270.1
2014/0066517 A1 * 3/2014 Grare ...................... A61K 31/04
                                                                  514/634

OTHER PUBLICATIONS

Guldi et al., "A Photosensitizer Dinuclear Ruthernium Complex:Intramolecular Energy Transfer to a Covalently Linked Fulleren Acceptor", Chemisty—A European Journal, 2001, 7, No. 8, p. 1597-1605.*
Armaroli et al, "Photophysical Properties of the ReI and RuII Complexes of a New C60-Substituted Bipyridine Ligand", Chemistry—A European Journal, 2002, 9, No. 10, p. 2314-2323.*

* cited by examiner

Figure 1 Pitch 44nm (22nm lines): 31.2 mJ/cm$^2$

Figure 2 Pitch 36nm (18 nm lines): 21.2mJ/cm$^2$

Figure 3: Pitch 50 (25nm lines): 48mJ/cm$^2$

Figure 4: line dosage of 575 pC/cm

Figure 5: line dosage of 575 pC/cm

Figure 6 line dosage of 600 pC/cm

Figure 7: Fitted response curves for K (ML296) and L (ML356). The sensitivity of K and L were 10.1 mC/cm$^2$ and 2.7 mC/cm$^2$, respectively.

Figure 8: 15.6 nm sparse line (top), 50 nm pitch dense lines (middle) and 40 nm pitch lines (bottom) for (a) K and (b) L

(a) (b)

Figure 9: Sparse line after 15s $SF_6:CHF_3$ etching (top) and 50 nm pitch dense lines after 30 nm $SF_6:CHF_3$ etching (bottom) for (a) K, (b) L

FULLERENES

FIELD OF INVENTION

The present disclosure relates to novel fullerene derivatives, positive and negative photoresist compositions prepared therefrom and methods of using them. The derivatives, their photoresist compositions and the methods are ideal for high speed, fine pattern processing using, for example, ultraviolet radiation, extreme ultraviolet radiation, beyond extreme ultraviolet radiation, X-rays, electron beam and other charged particle rays.

BACKGROUND

As is well known, the manufacturing process of various kinds of electronic or semiconductor devices such as ICs, LSIs and the like involves a fine patterning of a resist layer on the surface of a substrate material such as a semiconductor silicon wafer. This fine patterning process has traditionally been conducted by the photolithographic method in which the substrate surface is uniformly coated with a positive or negative tone photoresist composition to form a thin layer of the photoresist composition and selectively irradiating with actinic rays (such as ultraviolet light) through a photomask followed by a development treatment to selectively dissolve away the photoresist layer in the areas exposed or unexposed, respectively, to the actinic rays leaving a patterned resist layer on the substrate surface. The thus obtained patterned resist layer is utilized as a mask in the subsequent treatment on the substrate surface such as etching. The fabrication of structures with dimensions on the order of nanometers is an area of considerable interest since it enables the realization of electronic and optical devices, which exploit novel phenomena such as quantum confinement effects and also allows greater component packing density. As a result, the resist layer is required to have an ever increasing fineness which can be accomplished only by using actinic rays having a shorter wavelength than the conventional ultraviolet light. Accordingly, it is now the case that, in place of the conventional ultraviolet light, electron beams (e-beams), excimer laser beams, EUV, BEUV and X-rays are used as the short wavelength actinic rays. The minimum size obtainable is primarily determined by the performance of the resist material and the wavelength of the actinic rays. Various materials have been proposed as suitable resist materials. In the case of negative tone resists based on polymer crosslinking, there is an inherent resolution limit of about 10 nm, which is the approximate radius of a single polymer molecule.

It is also known to apply a technique called "chemical amplification" to the polymeric resist materials. A chemically amplified resist material is generally a multi-component formulation in which there is a main polymeric component, such as a novolac resin which contributes towards properties such as resistance of the material to etching and its mechanical stability and one or more additional components which impart desired properties to the resist and a sensitizer. By definition, the chemical amplification occurs through a catalytic process involving the sensitizer, which results in a single irradiation event causing exposure of multiple resist molecules. In a typical example the resist comprises a polymer and a photoacid generator (PAG) as sensitizer. The PAG releases a proton in the presence of radiation (light or e-beam), either directly or via a process mediated via other components in the resist. Such processes, for example, as in EUV and Ebeam exposures where the photon/electron typically interacts with the polymer (or fullerene/crosslinker) to generate a radical which then interacts with the PAG to create a proton. This proton can then for example react with the polymer to cause it to lose a functional group. In the process, a second proton is generated which can then react with a further molecule. The speed of the reaction can be controlled, for example, by heating the resist film to drive the reaction. After heating, the reacted polymer molecules are free to react with remaining components of the formulation, as would be suitable for a negative-tone resist. In this way the sensitivity of the material to actinic radiation is greatly increased, as small numbers of irradiation events give rise to a large number of exposure events.

In such chemical amplification schemes, irradiation results in cross-linking of the exposed resist material, thereby creating a negative tone resist. The polymeric resist material may be self-cross-linking or a cross linking molecule may be included. Chemical amplification of polymeric-based resists is disclosed in U.S. Pat. Nos. 5,968,712, 5,529,885, 5,981,139 and 6,607,870.

Various fullerene derivatives have been shown to be useful e-beam resist materials by the present inventors, Appl. Phys. Lett. volume 72, page 1302 (1998), Appl. Phys. Lett. volume 312, page 469 (1999), Mat. Res. Soc. Symp. Proc. volume 546, pace 219 (1999) and U.S. Pat. No. 6,117,617.

One area that is always of interest is the photospeed of photoresists. Higher photospeed means higher output, and in some cases, higher photospeed can mean improved resolution capabilities. Various methods and "tricks" have been used to increase the photospeed of both positive and negative working photoresists including addition of photocatalysts, photosensitizers and photoabsorbers.

As can be seen there is an ongoing desire to obtain finer and finer resolution of photoresists that will allow for the manufacture of smaller and smaller semiconductor devices in order to meet the requirements of current and further needs. It is also desirable to create materials, which can be used in conjunction with these photoresists, which will be more robust to the processes used to create current semiconductor devices, such as, for example, etching resistance. There is also an on-going desire to increase photospeed of lithographic photoresists.

SUMMARY OF THE DISCLOSURE

In a first embodiment disclosed and claimed herein is a photoresist composition containing a) at least one fullerene of the general formula:

wherein x is at least 10, y is 1-6, $R_1$ is a $C_1$ to $C_{30}$ branched or unbranched, substituted or unsubstituted alkyl, cycloalkyl, aryl, aralkyl, heterocyclic, alkylheterocyclic substituent or a substituent which coordinates with at least one metal, and $R_2$ is a substituent, which coordinates with at least one metal, and b) at least one solvent.

In a second embodiment disclosed and claimed herein is the photoresist of the above embodiment further including at least one photo acid generator, and at least one crosslinker, and $R_1$ may optionally also be a substituent which coordinates with at least one metal.

In a third embodiment disclosed and claimed herein are the photoresists of the above embodiments further comprising at least one alkali soluble resin and optionally a protected polymer containing an acid-labile group.

In a fourth embodiment, disclosed and claimed herein are the photoresist compositions of the above embodiments, wherein $R_1$ is a substituent which coordinates with at least one metal or $R_1$ is a —COO-alkyl-aryl-(CH2)n-O—$R_0$ substituent wherein, alkyl is a branched or unbranched, substituted or unsubstituted divalent alkyl chain of 1-16 carbons with or without one or more heteroatoms substituted into the chain, aryl is a substituted or unsubstituted divalent phenyl group, heteroaromatic group, or fused aromatic or fused heteroaromatic group, and $R_0$ is H or an acid labile group, the divalent alkyl chain may be a methylene, ethylene or 1,3-propylene group, the divalent alkyl chain may contain fluorine atoms, the aryl group may be a substituted or unsubstituted phenylene group, the acid labile group may be an alkoxycarbonyl group, and the heteroatoms are one or more of oxygen, nitrogen, sulfur, or oxides of sulfur.

In a fifth embodiment, disclosed and claimer herein is a photoresist composition containing a) at least one fullerene of the general formula:

wherein x is at least 10, y is 1-6 and $R_2$ is a substituent, which coordinates with at least one metal, and b) at least one solvent. The composition may further include at least one photo acid generator, and at least one crosslinker.

In a sixth embodiment disclosed and claimed herein is a photoresist composition containing a) at least one fullerene of the general formula:

wherein x is at least 10, y is 1-6, $R_1$ is a $C_1$ to $C_{30}$ branched or unbranched, substituted or unsubstituted alkyl, cycloalkyl, aryl, aralkyl, heterocyclic, alkylheterocyclic substituent or a substituent which coordinates with at least one metal, and at least one of $R_2$, $R_3$, $R_4$ and/or $R_5$ is a substituent which coordinates with at least one metal, the remaining $R_2$, $R_3$, $R_4$ and/or $R_5$ is/are H, a $C_1$ to $C_{30}$ branched or unbranched, substituted or unsubstituted alkyl, aryl, aralkyl, heterocyclic or alkylheterocyclic substituent, halogen, or chalogen, and b) at least one solvent. The compositions may further include at least one photo acid generator, and at least one crosslinker, and $R_1$ may optionally also be a substituent which coordinates with at least one metal.

In a seventh embodiment disclosed and claimed herein are the photoresists of the above embodiment further including at least one photo acid generator, and at least one crosslinker, and $R_1$ may optionally also be a substituent which coordinates with at least one metal.

In an eighth embodiment disclosed and claimed herein are photoresists of the above embodiments further comprising at least one alkali soluble resin and optionally a protected polymer containing an acid-labile group.

In a ninth embodiment, disclosed and claimed herein is a photoresist composition of the above embodiments, wherein at least one of $R_2$, $R_3$, $R_4$ and/or $R_5$ is a —COO-alkyl-aryl-(CH2)n-O—$R_0$ substituent, wherein alkyl is a branched or unbranched, substituted or unsubstituted divalent alkyl chain of 1-16 carbons with or without one or more heteroatoms substituted into the chain, aryl is a substituted or unsubstituted divalent phenyl group, heteroaromatic group, or fused aromatic or fused heteroaromatic group, and $R_0$ is H or an acid labile group, the divalent alkyl chain may be a methylene, ethylene or 1,3-propylene group, the divalent alkyl chain may contain fluorine atoms, the aryl may be a substituted or unsubstituted phenylene group, the acid labile group may be an alkoxycarbonyl group, and the heteroatoms may be one or more of oxygen, nitrogen, sulfur, or oxides of sulfur.

In an tenth embodiment, disclosed and claimed herein is a photoresist composition of the above embodiments, further containing at least one fullerene of the general formula:

wherein x is at least 10, y is 1-6, n is 0-1, alkyl is a branched or unbranched, substituted or unsubstituted divalent alkyl chain of 1-16 carbons with or without one or more heteroatoms substituted into the chain, aryl is a substituted or unsubstituted divalent phenyl group, heteroaromatic group, or fused aromatic or fused heteroaromatic group, and R is the same or different and is H or an acid labile group, wherein the crosslinker crosslinks at least with the fullerene when processed.

In an eleventh embodiment, disclosed and claimed herein are the photoresist compositions of the above embodiments, wherein the metal is a transition metal, alkali metal, alkaline earth metal, a lanthanide metal, an actinide metal, metalloids, as well as metal from groups 13, 14 and 15 of the periodic table and their respective cation, the substituent which coordinates with at least one metal is a monodentate or a polydentate ligand and the substituent which coordinates with at least one metal may be at least one of a bipyridyl, a crown ether, an ethylene diamine monomer or oligomer, a porphyrine, an ethylene diamine tetraacrylate, a peptide, a polysaccharide, phosphine, phosphates, carboxylates, and/or ethylene oxide monomers or oligomers, cyclic polyamines, and heterocycles.

In a twelfth embodiment, disclosed and claimed herein are the photoresist compositions of the above embodiments, wherein the acid labile group may be a tertiary alkoxycarbonyl group, wherein the at least one photoacid generator may be an onium salt compound, a triphenylsulfonium salt, a sulfone imide compound, a halogen-containing compound, a sulfone compound, a sulfonate ester compound, a quinonediazide compound, a diazomethane compound, an iodonium salt, an oxime sulfonate, or a dicarboxyimidyl sulfate and the at least one crosslinker may be an acid sensitive monomer or polymer.

In a thirteenth embodiment, disclosed and claimed herein are the photoresist compositions of the above embodiments, further containing at least one of a novolac, a polyhydroxystyrene, a polyacrylate, or a maleic anhydride ester-acid polymer crosslinking additive, the crosslinker may be at least one of a glycidyl ether, glycidyl ester, glycidyl amine, a methoxymethyl group, an ethoxy methyl group, a butoxymethyl group, a benzyloxymethyl group, dimethylamino methyl group, diethylamino methyl group, a dibutoxymethyl group, a dimethylol amino methyl group, diethylol amino methyl group, a dibutylol amino methyl group, a morpholino methyl group, acetoxymethyl group, benzyloxy methyl group, formyl group, acetyl group, vinyl group or an isopropenyl group, the crosslinker may be one or more glycidyl ether groups attached to a novolac resin, and the solvent comprises esters, ethers, ether-esters, ketones, ketoesters, hydrocarbons, aromatics, and halogenated solvents.

In a fourteenth embodiment, disclosed and claimed herein are the photoresist compositions of the above embodiments, further containing at least one fullerene comprising the general formula:

wherein x is at least 10, y is 1-6, a is 1-10 and R is H or an acid labile group and wherein the —$CH_2CH_2$—O— may be optionally substituted with fluorine atoms.

In a fifteenth embodiment, disclosed and claimed herein is a method of forming a patterned resist layer on a substrate including the steps of: providing a substrate, applying the photoresist composition of any the above embodiments to a desired wet thickness, heating the coated substrate to form a dried coating to obtain a desired thickness, imagewise exposing the coated substrate to actinic radiation, optionally heating the imagewise exposed coated substrate, and removing the unexposed or exposed areas of the coating using an aqueous or non-aqueous developer composition, wherein the remaining coating is optionally heated. The actinic radiation of the method can be ultraviolet, deep ultraviolet, extreme ultraviolet, x-ray, ion beam or electron beam.

In a sixteenth embodiment, disclosed and claimed herein is a fullerene of the general formula:

wherein x is at least 10, y is 1-6, $R_1$ is a $C_1$ to $C_{30}$ branched or unbranched, substituted or unsubstituted alkyl, cycloalkyl, aryl, aralkyl, heterocyclic or alkylheterocyclic substituent or a substituent which coordinates with at least one metal, and $R_2$ is a substituent which of coordinates with at least one metal and $R_1$ may optionally be a substituent which of coordinates with at least one metal.

In a seventeenth embodiment, disclosed and claimed herein is the fullerene of the above embodiment, wherein $R_1$ is a substituent which coordinates with at least one metal or $R_1$ is a —COO-alkyl-aryl-(CH2)n-O—$R_0$ substituent wherein, alkyl is a branched or unbranched, substituted or unsubstituted divalent alkyl chain of 1-16 carbons with or without one or more heteroatoms substituted into the chain, aryl is a substituted or unsubstituted divalent phenyl group, heteroaromatic group, or fused aromatic or fused heteroaromatic group, and $R_0$ is H or an acid labile group, the divalent alkyl chain may be a methylene, ethylene or 1,3-propylene group, the divalent alkyl chain may contain fluorine atoms, the aryl group may be a substituted or unsubstituted phenylene group, the acid labile group may be an alkoxycarbonyl group, and the heteroatoms are one or more of oxygen, nitrogen, sulfur, or oxides of sulfur.

In an eighteenth embodiment, disclosed and claimer herein is a fullerene of the general formula:

wherein x is at least 10, y is 1-6 and $R_2$ is a substituent which of coordinates with at least one metal, at least one photo acid generator, at least one crosslinker, and at least one solvent.

In a nineteenth embodiment disclosed and claimed herein is a fullerene of the general formula:

wherein x is at least 10, y is 1-6, $R_1$ is a $C_1$ to $C_{30}$ branched or unbranched, substituted or unsubstituted alkyl, cycloalkyl, aryl, aralkyl, heterocyclic, alkylheterocyclic substituent or a substituent which coordinates with at least one metal, and at least one of $R_2$, $R_3$, $R_4$ and/or $R_5$ is a substituent which coordinates with at least one metal, the remaining $R_2$, $R_3$, $R_4$ and/or $R_5$ is/are H, a $C_1$ to $C_{30}$ branched or unbranched, substituted or unsubstituted alkyl, aryl, aralkyl, heterocyclic or alkylheterocyclic substituent, halogen, or chalogen, $R_1$ may optionally also be a substituent which coordinates with at least one metal.

In a twentieth embodiment, disclosed and claimed herein is a fullerene of the above embodiments, wherein at least one of $R_2$, $R_3$, $R_4$ and/or $R_5$ is a —COO-alkyl-aryl-(CH2)n-O—$R_0$ substituent, wherein alkyl is a branched or unbranched, substituted or unsubstituted divalent alkyl chain of 1-16 carbons with or without one or more heteroatoms substituted into the chain, aryl is a substituted or unsubstituted divalent phenyl group, heteroaromatic group, or fused aromatic or fused heteroaromatic group, and $R_0$ is H or an acid labile group, the divalent alkyl chain may be a methylene, ethylene or 1,3-propylene group, the divalent alkyl chain may contain fluorine atoms, the aryl may be a substituted or unsubstituted phenylene group, the acid labile group may be an alkoxycarbonyl group, and the heteroatoms may be one or more of oxygen, nitrogen, sulfur, or oxides of sulfur.

In a twenty-first embodiment, disclosed and claimed herein is a fullerene of the above embodiments, wherein the metal is a transition metal cation, alkali cation, alkaline earth cation, a lanthanide cation, an actinide cation, metalloids, as well as cations from groups 13, 14 and 15 of the periodic table, the substituent which coordinates with at least one metal is a monodentate or a polydentate ligand and the substituent which coordinates with at least one metal may be a bipyridyl, a crown ether, an ethylene diamine monomer or oligomer, a porphyrines, an ethylene diamine tetraacrylate, a peptide, a polysaccharide, phosphine, phosphates, carboxylates, and/or ethylene oxide monomers or oligomers, cyclic polyamines, and heterocycles.

In all the above embodiments, the fullerene may be substituted with more than one type of ligand, and the metal may contain ligands that are not bonded to the fullerene.

In other embodiments the fullerenes of the above embodiments may contain one or more the following substituents:

wherein alkyl is a branched or unbranched, substituted or unsubstituted divalent alkyl chain of 1-16 carbons with or without one or more heteroatoms substituted into the chain, aryl is a substituted or unsubstituted divalent phenyl group, heteroaromatic group, or fused aromatic or fused heteroaromatic group, and R is the same or different and is H or an acid labile group.

In further embodiments the fullerenes of the above embodiments may contain one or more the following substituents:

wherein a is 1-10 and R is H or an acid labile group and wherein the —CH$_2$CH$_2$—O— may be optionally substituted with fluorine atoms.

DETAILED DESCRIPTION

As used herein, the conjunction "and" is intended to be inclusive and the conjunction "or" is not intended to be exclusive unless otherwise indicated. For example, the phrase "or, alternatively" is intended to be exclusive.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

As used herein, the terms "dry", "dried" and "dried coating" means having less than 8% residual solvent.

As used herein the term "protected polymer" means a polymer which is used in the chemical amplification process, such polymer containing acid-labile functionality so that when exposed to an acid the functionally it giving a polymer with different functionality.

It has surprisingly been found that photoresists have increased photospeed when they contain the metal liganded fullerenes described in the current disclosure. Not to be held to theory but it is believed that the metal atom or cation acts to enhance the generation of secondary electrons during the exposure process, which, in a composition containing materials with acid-labile functionalities or other chemical amplification schemes, would indirectly enhance the production of acid, due to a high levels of secondary electrons, whilst in a non-chemically amplified resist increase secondary electron generation would lead to increased direct exposure events. Increases of 2 to 10 times have been obtained when the fullerenes of the current disclosure were used alone or incorporated into positive or negative photoresists.

One method of incorporating metals for these compositions is for them to be coordinated to the fullerenes which are used in fullerene containing photoresists, but which could also be added to non-fullerene resists as a sensitizing agent. Fullerenes having pendent substituents which function as ligands for coordinating with metals can be prepared and added to the photoresists.

There are a plethora of materials that can be used to coordinate metals, also known as ligands. Ligands are generally derived from charge-neutral precursors and are represented by oxides, amines, phosphines, sulfides, carboxylic acid, esters, hydroxys, alkenes, and then like. Denticity refers to the number of times a ligand bonds to a metal through non-contiguous donor sites. Many ligands are capable of binding metal ions through multiple sites, usually because the ligands having lone pairs on more than one atom. Ligands that bind via more than one atom are often termed chelating. A ligand that binds through two sites is classified as bidentate and three sites as tridentate, etc. Chelating ligands are commonly formed by linking donor groups via organic linkers. Examples include ethylenediamine include A classic bidentate ligand which is derived by the linking of two ammonia groups with an ethylene (—CH$_2$CH$_2$—) linker. A classic example of a polydentate ligand is the hexadentate chelating agent EDTA, which is able to bond through six sites, completely surrounding some metals.

Complexes of polydentate ligands are called chelate complexes. They tend to be more stable than complexes derived from monodentate ligands. When the chelating ligand forms a large ring that at least partially surrounds the central metal and bonds to it, leaving the central atom at the center of a large ring. The more rigid and the higher its denticity, the more stable will be the macrocyclic complex, for example, heme: the iron atom is at the center of a porphyrin macrocycle, being bound to four nitrogen atoms of the tetrapyrrole macrocycle. The very stable dimethylglyoximate complex of nickel is a synthetic macrocycle derived from the anion of dimethylglyoxime.

The current application discloses photoresist composition s containing one or more of the fullerenes of the following structures A, B and C;

A

B

C x is at least 10, such as, for example, 10, 25, 30, 35, 38, 39, 41, 42, 45 and 48 wherein the example fullerene core is $C_{20}$, $C_{50}$, $C_{60}$, $C_{70}$, $C_{76}$, $C_{78}$, $C_{82}$, $C_{84}$, $C_{90}$ and $C_{96}$. y is between about 1 to about 6 representing the number of substituents on the fullerene. As is well known in the industry, manufacture of such materials often results in mixtures of the number of substitutions such that a useful material may have, for example, y=2.35 or 5.1 representing an average of a mixture of substitutions. Thus y is not meant to be an absolute number of substituents but an average thereof.

$R_1$ is a $C_1$ to $C_{30}$ branched or unbranched, substituted or unsubstituted alkyl, cycloalkyl, aryl, aralkyl, heterocyclic, alkylheterocyclic substituent or a substituent which coordinates with at least one metal.

The alkyl group can be a branched or unbranched divalent alkyl chain of 1-16 carbons with or without heteroatoms substituted into the chain. As used herein alkyl also includes any unsaturations in the chain such an olefin group, such as for example, —CH=CH—, or an alkynyl group. As mentioned the alkyl group may have heteroatoms substituted into the chain as part or the chain, such as O, N, S, S=O or $SO_2$ and the like, such as, for example, —($CH_2CH_2$—O)$_z$— wherein z is between about 1 and about 16, or —($CH_2CH_2NH$)$_w$— wherein w is between about 1 and about 16, and the like. Also included are branched alkyl groups that contain heteroatoms in the ring, such as, for example —($CH_2CH_2NR''$)$_v$— wherein R" can be a branched or unbranched divalent alkyl chain of 1-16 carbons with or without heteroatoms substituted into the R" chain.

Aryl is a substituted or unsubstituted divalent aromatic group, such aromatic groups include, for example the phenylenes (—$C_6H_4$—), the fused divalent aromatic group, such as, for example, the naphthylenes (—$C_{10}H_6$—), the anthacenylenes (—$C_{14}H_8$—) and the like, as well as the heteroaromatic groups, such as, for example, the nitrogen heterocycles: pyridines, quinolines, pyrroles, indoles, pyrazoles, the triazines, and other nitrogen-containing aromatic heterocycles well known in the arts, as well as the oxygen heterocycles: furans, oxazoles and other oxygen-containing aromatic heterocycles, as well the sulfur containing aromatic heterocycles, such as, for example, thiophenes.

$R_2$ is a substituent which can coordinate with at least one metal. As mentioned above there are a large number of materials that can be used as substituents that will coordinate with metals. Some examples include, substituted and unsubstituted bipyridyls, a crown ethers, ethylene diamine monomers or oligomers, porphyrines, ethylene diamine tetraacrylates, peptides, polysaccharides, phosphines, phosphates, carboxylates, and/or ethylene oxide monomers or oligomers, cyclic polyamines, and fused heterocycles.

The one or more metals that coordinates with the fullerene are any metal capable of coordination, such as, for example, a transition metal cation, alkali cation, alkaline earth cation, a lanthanide cation, an actinide cation, metalloids, as well as cations from groups 13, 14 and 15 of the periodic table. Further examples include Fe, Co, Ni, Cu, Zn, Ru, Rh, Pd, Ag, Cd, Ir, Pt, Au, W, Mo, Hf, Cr and Zr.

In fullerene A, above, $R_1$ and $R_2$ may be the same in that both substituents may be substituents that can coordinate with metals. They may be different but capable of coordinating different metals depending on their structure.

In fullerene C, above, any combination of $R_1$ through $R_5$ may be a substituent that can coordinate with metals. Again, they may coordinate with different metals depending on their structure, so that there could be 5 different metals coordinated to one fullerene molecule.

The fullerenes of the current disclosure may also be substituted with other groups that introduce certain desired characteristics to the fullerene such as, for example, solubility in certain solvents or compatibility with certain components of the formulation. The fullerenes of the current disclosure may be substituted with groups that contain acid labile functionality. These functionalities may be deblocked when exposed to radiation induced acid to give a functional group that provides other properties, such as, for example, a phenol OH which can be soluble in an alkaline solution or can react with crosslinkers. The fullerenes can be prepared by any of a number of methods, such as, for example, the procedure as shown in the examples below.

In embodiments which contain at least one photo acid generator (PAG) suitable PAGs for the photoresists of the current disclosure include onium salt compounds, sulfone imide compounds, halogen-containing compounds, sulfone compounds, ester sulfonate compounds, quinone diazide compounds, and diazomethane compounds. Specific examples of these acid generators are indicated below.

The compositions of the current disclosure may or may not contain one or more of the above mentioned photoacid generators, as the metal containing fullerene may be used alone in only a solvent.

When crosslinkers are used in the compositions of the current disclosure, those that are suitable constitute compounds able to cross-link with the one of the fullerene components during the process such that when the fullerene is substituted with a phenol or similar group, such as, for example, an alkyl —OH group, or when the fullerene is deprotected to provide for a phenol or similar group, the crosslinker will react with the —OH group situated on the phenol or similar group. Examples of crosslinkers include compounds comprising at least one type of substituted group that possess a cross-linking reactivity with the phenol or similar group of the fullerene. Specific examples of this crosslinking group include the epoxies, glycidyl ether group, glycidyl ester group, glycidyl amino group, methoxymethyl group, ethoxy methyl group, benzyloxymethyl group, dimethylamino methyl group, diethylamino methyl group, dimethylol amino methyl group, diethylol amino methyl group, morpholino methyl group, acetoxymethyl group, benzyloxy methyl group, formyl group, acetyl group, vinyl group and isopropenyl group.

Examples of compounds having the aforementioned cross-linking substituted group include, for example, bisphenol A-based epoxy compounds, bisphenol F-based epoxy compounds, bisphenol S-based epoxy compounds, novolac resin-based epoxy compound, resol resin-based epoxy compounds, poly (hydroxystyrene)-based epoxy compounds, methylol group-containing melamine compounds, methylol group-containing benzoguanamine compounds, methylol group-containing urea compounds, methylol group-containing phenol compounds, alkoxyalkyl group-containing melamine compounds, alkoxyalkyl group-containing benzoguanamine compounds, alkoxyalkyl group-containing urea compounds, alkoxyalkyl group-containing phenol compounds, carboxymethyl group-containing melamine resins, carboxy methyl group-containing benzoguanamine resins, carboxymethyl group-containing urea resins, carboxymethyl group-containing phenol resins, carboxymethyl group-containing melamine compounds, carboxymethyl group-containing benzoguanamine compounds, carboxymethyl group-containing urea compounds, and carboxymethyl group-containing phenol compounds, methylol group-containing phenol compounds, methoxymethyl group-containing melamine compounds, methoxymethyl group-containing phenol compounds, methoxymethyl group-containing glycol-uril compounds, methoxymethyl group-containing urea compounds and acetoxymethyl group-containing phenol compounds. The methoxymethyl group-containing melamine compounds are commercially available as, for example, CYMEL300, CYMEL301, CYMEL303, CYMEL305 (manufactured by Mitsui Cyanamid), the methoxymethyl group-containing glycol-uril compounds are commercially available as, for example, CYMEL117 4 (manufactured by Mitsui Cyanamid), and the methoxymethyl group-containing urea compounds are commercially available as, for example, MX290 (manufactured by Sanwa Chemicals).

Examples of suitable solvents for the current disclosure include ethers, esters, ether-esters, ketones and ketone-esters Various additives may be added to the photoresist formulations to provide certain desirable characteristic of the photoresist such as, for example, acid diffusion control agents to retard acid from migrating into unexposed areas of the coating, surfactants to improve coating of substrates, adhesion promoters to improve adhesion of the coating to the substrate and sensitizers to improve the photosensitivity of the photoresist coating during photoexposure, and anti-foaming agents and air release agents, as well as other materials well known in the coatings industry.

The compositions disclosed and claimed herein may include other fullerene of general formulation D:

R may be H or D or an acid labile group. As used herein, examples of acid labile groups, include, for example, substituted methyl groups, 1-substituted ethyl groups, 1-substituted alkyl groups, silyl groups, germyl groups, alkoxycarbonyl group, acyl groups and cyclic acid-dissociable groups.

The alkoxycarbonyl acid labile groups include the methoxycarbonyl group, ethoxy carbonyl group, isopropoxy carbonyl group and t-butoxycarbonyl group.

In the above structure D, above, n may be 0 or 1. In the case where n=1, the fullerene contains a benzyl alcohol which will crosslink with the crosslinkers when processed. Additionally, in a further embodiment, when the benzyl alcohol is protected with the acid labile groups of the current disclosure, a reactive benzyl alcohol will be obtained when deprotected and, as above, will crosslink with the crosslinkers when processed.

In other embodiments other fullerenes are added to provide various desired properties such as improved sensitivity to the actinic radiation or for improvements in line edge roughness. Examples of such fullerenes include structure E:

wherein x, y and R are described above for structure D and R can include a carboxylic acid derivative which together with the $-(CH_2CH_2-O)_a$ provides for a carboxylic ester structure. The $-(CH_2CH_2-O)$ group may be substituted with fluorine atoms. a can be from about 1 to about 10.

The components of the compositions of the current disclosure are included in ranges as follows based on weight/weight: fullerenes from about 1% to about 100%, cross-linker from about 0% to about 80%, photoacid generator from about 0% to about 50%. The percent solids of the composition may range from about 0.001%-about 25%.

The photoresist compositions can be coated onto substrate such as a silicon wafer or a wafer coated with silicon dioxide, aluminium, aluminum oxide, copper, nickel, any of a number of semiconductor materials or nitrides or other substrates well known the semiconductor industry, or a substrate having thereon an organic film, such as, for example, a bottom layer anti-reflective film or the like. The photoresist compositions are applied by such processes as spin coating, curtain coating, slot coating, dip coating, roller coating, blade coating and the like. After coating, the solvent is removed to a level wherein the coating can be properly exposed. In some cases a residual of 5% solvent may remain in the coating while in other cases less than 1% is required. Drying can be accomplished by hot plate heating, convection heating, infrared heating and the like. The coating is imagewise exposed through a mask containing a desired pattern, or via a software generated pattern in the case of "maskless lithography" such as electron beam lithography.

Radiation suitable for the described photoresist compositions include, for example, ultraviolet rays (UV), such as the bright line spectrum of a mercury lamp (254 nm), a KrF excimer laser (248 nm), and an ArF excimer laser (193 nm), extreme ultraviolet (EUV) such as 13.5 nm from plasma discharge and synchrotron light sources, beyond extreme ultraviolet (BEUV) such as 6.7 nm exposure, X-ray such as synchrotron radiation. Ion beam lithography and charged particle rays such as electron beams may also be used.

Following exposure, the exposed coated substrate may optionally be post exposure baked to enhance the reaction of the photoacid generator, such as, for example, heating from about 30 to about 200° C. for about 10 to about 600 seconds. This may be accomplished by hot plate heating, convection heating, infrared heating and the like. The heating may also be performed by a laser heating processes such as, for example, a $CO_2$ laser pulse heating for about 2 to about 5 milliseconds. Both heating processes may be combined in tandem.

A flood exposure process may be applied after the pattern exposure to aid in further cure. Results have indicated that flood exposure reduces or eliminates pattern collapse after development of the negative-tone resists as well as reduction in line edge roughness. For example, a 532 nm continuous wave laser exposes the previously exposed resist for 1-2 sec followed by wet development. The flood process may or may not be followed by a heating step.

The unexposed areas are next moved using a developer, (when the photoresist composition is positive working the exposed areas are removed by the developer). Such developers include organic solvents as well as aqueous solution such as aqueous alkali solution. When an organic solvent is used to remove the unexposed areas generally the solvent is less aggressive than the solvent that was used in preparing the photoresist composition. Examples of aqueous alkali development solution include, for example, at least one type of alkaline compound such alkali metal hydroxides, ammonia water, alkylamines, alkanolamines, heterocyclicamines, tetraalkyl ammonium hydroxides, cholines, and 1,8-diazabicyclo[5.4.0]-7-undecan, 1,5-diazabicyclo[4.3.0]-5-nonene at a concentration of about 1 to about 10% by weight, such as, for example, about 2 to about 5% by weight. Water-soluble organic solvents such as methanol and ethanol and surfactants may also be added in suitable amounts to the alkaline aqueous solution, depending on the desired development characteristics and process parameters.

After development a final baking step may be included to further enhance the curing of the now exposed and developed pattern. The heating process may be, for example, from about 30 to about 600° C. for about 10 to about 120 seconds and may be accomplished by hot plate heating, convection heating, infrared heating and the like.

EXAMPLES

Synthesis Example A (Preparation of Structure C Above)

4'-methyl-2,2'-bipyridine-4-carboxaldehyde F was synthesized according to the literature reported procedures (G. Strouse, J. Schoonover, R. Duesing, S. Boyde, W. Jones, T. Meyer, Inorg. Chem., 1995, 34, 473-487)

F

Pt(DMSO)2Cl₂ G were synthesised according to the literature reported procedures (J. Price, A. Williamson, R. Schramm, B. Wayland, Inorg. Chem., 1972, 11, 1280-1284)

N-((3,5-di-tert-Butylphenyl)methyl)glycine methyl ester H

H

Glycine methyl ester hydrochloride (0.37 g) and 3,5-di-tert-butylbenzaldehyde (0.50 g) were degassed with Ar and suspended in dry CH₂Cl₂ (15 mL). Et3N (0.41 mL) was added, and the resulting solution was stirred at room temperature for 17 hours in the presence of 4 Å molecular sieves. The molecular sieves and resulting precipitate were then removed by filtration, the filtrate was concentrated to 10 mL, and Na[B(OAc)₃H] (0.63 g) and glacial acetic acid (2 mL) were added, and the resulting suspension was left to stir at room temperature for 17 h. The solvent was then removed under reduced pressure and the resulting mixture was dissolved in MeOH (5 mL), cooled to 0° C., and NaHCO₃ solution was slowly added until the mixture reached pH 7. The resulting solution was extracted into CH₂Cl₂ (4×15 mL), the organic fractions were then combined, washed with water (10 mL) and dried over MgSO₄. After removal of MgSO₄ the resulting solution was concentrated and purified by column chromatography (silica gel, petroleum ether/ethyl acetate 10:1, then 10:2) to give the product (0.49 g, 73%) as a colourless oil.

N-((3,5-di-tert-Butylphenyl)methyl)glycine J

J

N-((3,5-di-tert-Butylphenyl)methyl)glycine methyl ester (0.49 g) was dissolved in MeOH (10 mL), NaOH (150 mg) was added, and the reaction mixture was left to stir at room temperature for 72 hours. The solvent was removed under reduced pressure, the resulting solid dissolved in water (5 mL), and a 1M HCl solution was added dropwise to adjust the pH to 6.7. The resulting white precipitate filtered, washed sequentially with water (3×5 mL) then acetone (1 mL) and dried in air to give the product (0.32 g, 70%) as a white powder.

4-methyl, 4'-(2-(N-(3,5-di-tert-butylphenylmethyl)) fulleropyrrolidino)-bipyridine K

K

C60 fullerene (100 mg obtained from SES Research), N-((3,5-di-tert-butylphenyl)methyl)glycine (46 mg) and 4'-methylbipyridine-4-carboxaldehyde (33 mg) were degassed with Ar and dissolved in dry toluene (60 mL). The resultant mixture was sonicated for 15 min, degassed with bubbling Ar for 15 minutes and then heated at reflux for 2 hours. The solvent was then removed under reduced pressure, and the resulting solid was purified by column chromatography (silica gel: toluene, then toluene/ethyl acetate 99:1). Further purification was carried out by suspending the solid in MeOH (20 mL), filtering, washing with MeOH (30 mL) and drying under vacuum to give the desired product as a black solid (68 mg, 43%).

4-methyl,4'-(2-(N-(3,5-di-tert-butylphenylmethyl)) fulleropyrrolidine)-bipyridine Pt dichloride L (Structure C)

L

4-methyl,4'-(2-(N-(3,5-di-tert-butylphenylmethyl))fulleropyrrolidine)-bipyridine (20 mg) and Pt(DMSO)$_2$Cl$_2$ (8 mg) were degassed together with Ar and dissolved in degassed CHCl$_3$ (15 mL). The resultant mixture was then heated to reflux under Ar atmosphere for 4 hours. The solvent was then removed under reduced and the resulting solid was purified by column chromatography (silica gel, under N$_2$ pressure, CH$_2$Cl$_2$, then CH$_2$Cl$_2$/MeOH 99.5:0.5) and dried under vacuum to give the product (22 mg, 89%) as a brown solid.

Synthesis Example(Preparation of Structure D Above)

Fullerene I: [3-(4-t-butoxycarbonyl)phenyl-1-propyl malonate]-methano-[60]fullerene Synthesis of 3-(4-t-butoxycarbonyl)phenyl-1-propanol (1): To a 250 mL round bottom flask was added 3-(4-hydroxyphenyl)-1-propanol (10 g, 65.7 mmol), dichloromethane (75 mL) and di-tert-butyldicarbonate (14.36 g, 65.7 mmol). The mixture was stirred under nitrogen and cooled to 0° C. in an ice bath. Potassium carbonate (24.37 g, 176 mmol) and 18-crown-6 (0.90 g, 3.4 mmol) dissolved in dichloromethane were added. The resulting mixture was stirred and warmed to room temperature overnight. The crude reaction mixture was filtered through a silica gel and rinsed with ethyl acetate. The resulting solvent was evaporated and the residue was purified via flash column chromatography on silica gel with ethyl acetate: hexane (40%) as eluant. The third fraction was combined and the solvent removed to give 15.7 g (yield: 95%) of 1 as a yellow oil. The product was characterized by $^1$H NMR and MS.

Synthesis of 3-(4-t-butoxycarbonyl)phenyl-1-propyl malonate (2): Dichloromethane (275 mL) was added to 1 (13.71 g, 54.4 mmol) in a 500 mL round bottom flask. To this was added, with stirring, pyridine (5.72 g, 72.35 mmol, 1.33 equiv) and the solution was cooled to 0° C. in an ice bath under nitrogen. Malonyl dichloride (2.65 mL, 27.2 mmol, in dichloromethane solution) was dropwise added. The initially clear solution became dark red upon complete addition of the malonyl dichloride. The mixture was stirred and warm up to room temperature overnight, upon which time it have become dark blue/green in color. The mixture was filtered through silica gel with ethyl acetate. The filtrate was evaporated and the residue was purified via flash column chromatography on silica gel using ethyl acetate as eluent. The fractions were collected and removed solvent to give 2 as yellow oil (9.56 g, 61% yield). The product was characterized by $^1$H and MS.

3

Synthesis of [3-(4-t-butoxycarbonyl)phenyl-1-propyl malonate]-methano-[60]fullerene(3): In a round bottom flask, [60]fullerene (1 equivalent), 9,10-dimethylancethracene (22 equivalent) and toluene were added. The resulting solution was stirred under $N_2$ for one hour to completely dissolve the fullerene. Carbon tetrabromide (22 equivalent) and 2 (22 equiv) were added to the solution. 1,8-Diazabicyclo[5.4.0]undec-7-ene (108 equivalent) was added dropwise and the resulting mixture was stirred at room temperature overnight and the initial purple solution had become a dark red color. The crude mixture was poured though silica gel with toluene to remove unreacted [60]fullerene, and then rinsed with dichloromethane:ethyl acetate:methanol (2:2:1) to remove the red/brown band containing the crude products. The solvents were evaporated and the resulting residue 3 (dark red/brown oil) was obtained and characterized by $^1$H NMR and MALDI MS. Major components in 3 is multi-adducts fullerenes (n=4 to 6).

Synthesis Example B

Fullerene II: (3-phenol-1-propyl malonate)-methano-[60]fullerene

4

Synthesis of (3-phenol-1-propyl malonate)-methano-[60] fullerene (4): In a 50 mL round bottom flask, 3 was dissolved in dichloromethane (10 mL) and stirred under nitrogen. Triflic acid (0.1 mol %) was added and stirred for 4 hours. The solvent was removed under vacuum and the resulting residue 4 was obtained and characterized by $^1$H NMR and MALDI MS.

Sample Preparation

All of the samples for SEM characterisation used silicon chips diced from a 4-inch wafer as substrates. The chips were cleaned with a 15 min ultrasonic wash in acetone followed by another 15 min in isopropyl alcohol (IPA). The substrates were subsequently dried with nitrogen before spin coating. The fullerene derivatives (Structures K and L above) were dissolved in chloroform with a concentration of 5 gl$^{-1}$. By adjusting the spin speed, a 30-50 nm resist film was prepared for sensitivity tests while a 20-30 nm film for high-resolution tests. A 70° C./10 min post-application bake (PAB) was applied after spin coating.

Electron Beam Lithography and SEM Characterisation

An FEI XL30 SFEG field emission scanning electron microscope with an ELPHY Plus pattern generator (Raith) was used for e-beam patterning. For the sensitivity and contrast evaluation, a beam voltage of 20 keV was used to pattern a set of 30×30 squares with various electron doses. The remained film thickness of each square after developing was measured using a surface profiler (Dektak 3st Auto). A logistic function was used to fit the thickness-dose plot to extract the sensitivity (dose at 50% remaining film thickness) and contrast (the slope of the linear rising portion of the curve). For the high-resolution patterning, 30 kV acceleration voltage was used with around 50 pA beam current. Single pixel lines were patterned in these tests and the dosage was described as a line dose (μC/cm). After exposure, a dip development in monochlorobenzene (MCB) for 20 s followed by a rinse in IPA for several seconds was applied.

The high-resolution structures on silicon substrate were imaged using the same SEM with 5 kV acceleration voltage. The line width roughness (LWR) of line patterns was measured using SuMMIT.

Sensitivity and Resolution Evaluation

Figure 7:
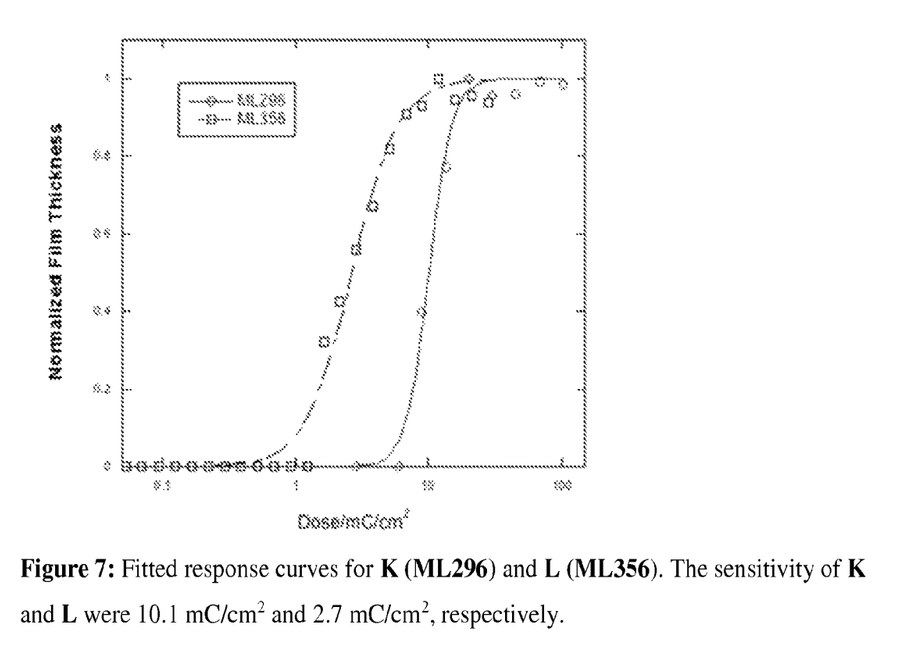
FIG. 7: shows the sensitivities of K and L under 20 kV electron beam exposure

As shown in FIG. 7, the sensitivities of K and L under 20 kV electron beam were evaluated by fitting a response curve as described in the Experimental section. The sensitivity of structure K was 10.1 mC/cm$^2$, while the sensitivity of structure L was 2.7 mC/cm$^2$, showing a significant improvement after the introduction of Pt. The contrast of K was 2.9 whilst the L was 1.4.

Figure 3:
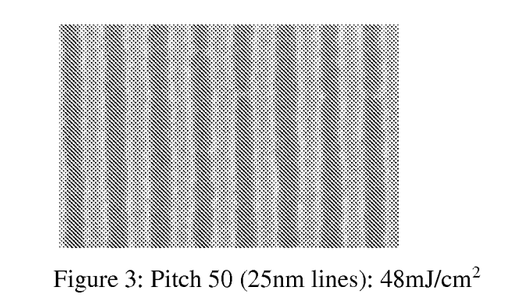
FIG. 3: shows an SEM showing the resolution obtained from example 3.
Figure 8:
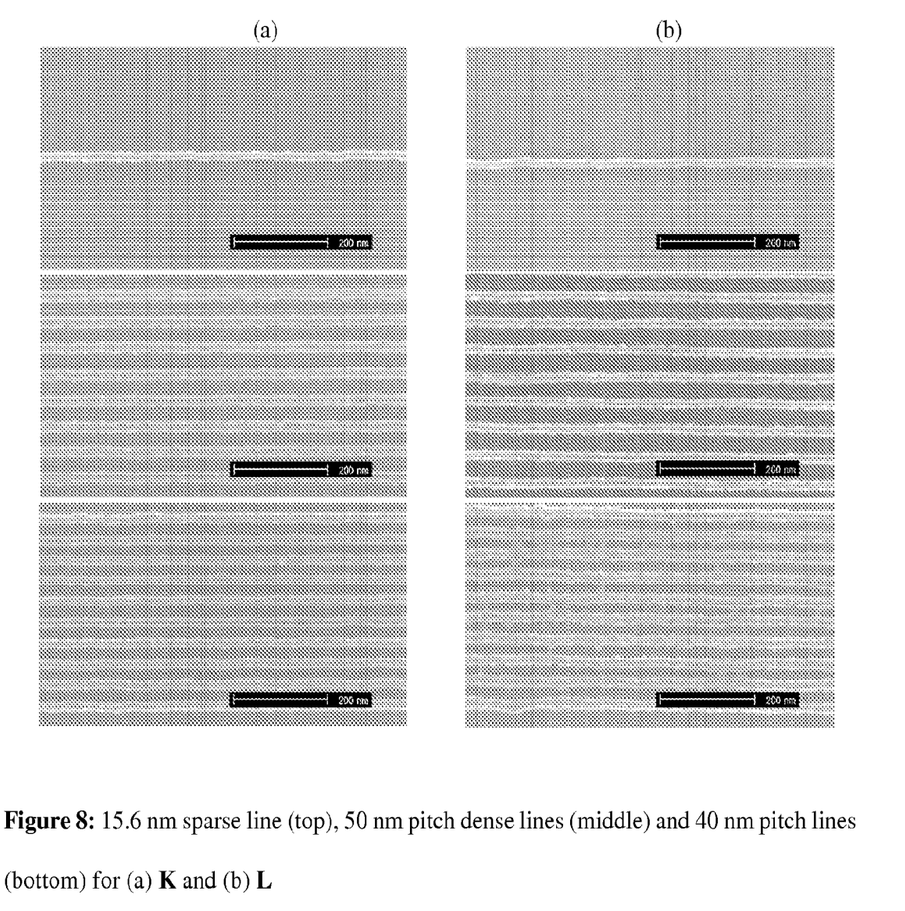
FIG. 8: shows the quality of lines from L and K

To evaluate the resolution capability of the materials, a series of single pixel lines with various pitch sizes were patterned at 30 kV electron beam. FIG. 3 shows the SEM images of sparse line, 50 nm pitch dense lines and 40 nm pitch dense lines for K and L. Sparse lines with 15.6 nm line width were obtained from both materials. The line dose of K was 47 μC/cm while the dose of L was 33 μC/cm. 50 nm pitch dense lines were achieved without pattern collapse or bridging. However, as shown in FIG. 8, the quality of lines from L is not as good as that from K. The LWRs (3σ) of K and L were measured to be 3.42 nm and 4.14 nm, respectively. 40 nm pitch dense lines were clearly resolved at K sample with around 1:1 lines and space ratio. However, considerable bridging was observed for L at this pitch size. See FIG. 8.

Plasma Etching Test

Figure 9:
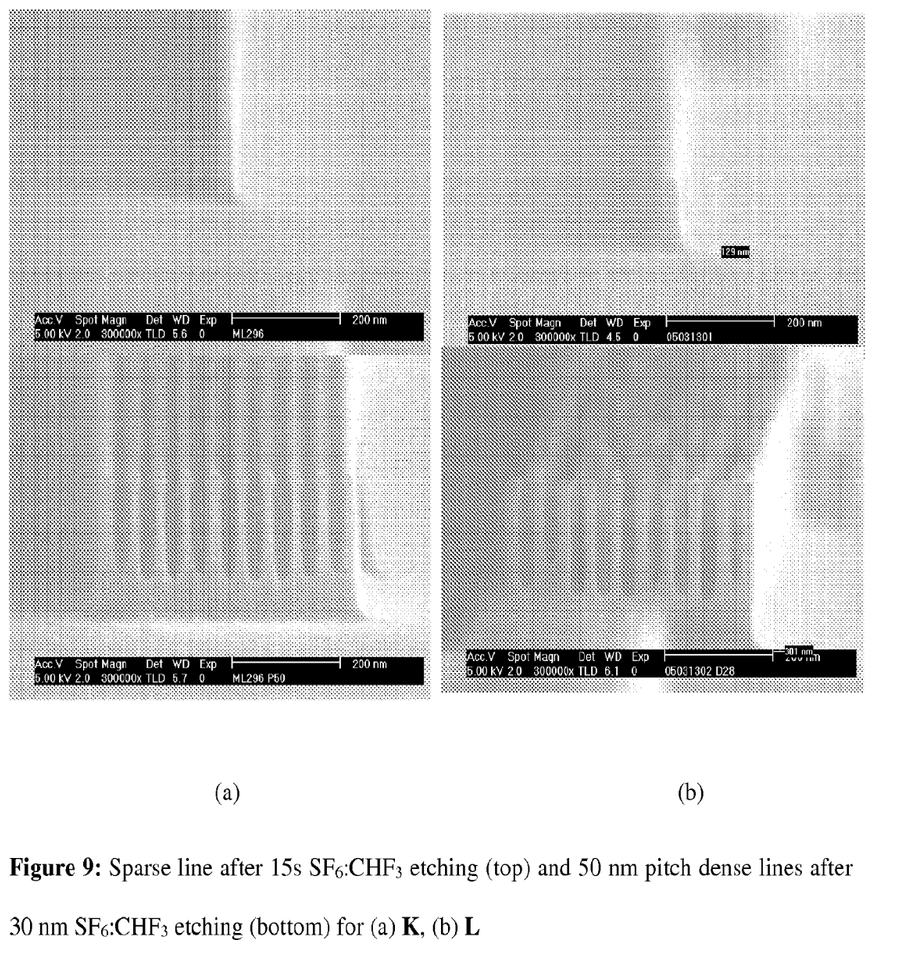
FIG. 9: shows SEMs of resolution after etching of structures K and L.

The etch resistance of K and L was investigated using electron cyclotron resonance (ECR) microwave plasma etching with SF$_6$:CHF$_3$ as etchants. Patterns of large areas and fine lines were examined to valuate the etch selectivity and capability of high-resolution pattern transfer. High etch selectivity was found for both of the materials. The ratios of exposed K and L etch rate to silicon substrate were 13.36 and 9.56, respectively. See FIG. 9.

Composition Example 1

Figure 1:
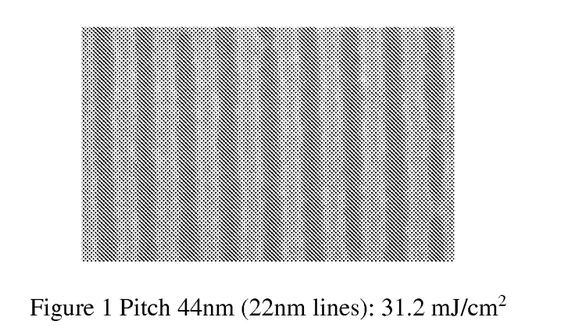
FIG. 1: shows an SEM showing the resolution obtained from example 1.

Into 100 mL of propylene glycol monomethyl ether (PGME) was added 0.25 g of fullerene I, 0.50 g of poly[(o-cresyl glycidyl ether)-co-formaldehyde] and 0.25 g of triphenylsulfonium hexafluoroantimonate and stirred for 1 hr at room temperature. The composition was applied to a silicon wafer and spin coated at 500 rpm for 5 sec followed by 2000 rpm for 60 sec. The coated wafer was then heated on a hot plate at 75° C. for 5 min to give a film of approximately 25 nm. The wafer was imagewise exposed to synchrotron based EUV light at 13-14 nm wavelength at 31.2 mJ/cm$^2$ and post exposure baked at 90° C. for 3 min. The unexposed areas were removed by puddle development in a 50:50 blend of monochlorobenzene and isopropyl alcohol for 20 sec followed by an isopropyl alcohol rinse. FIG. 1 shows the resulting 22 nm lines and spaces for example 1.

Composition Example 2

Figure 2:
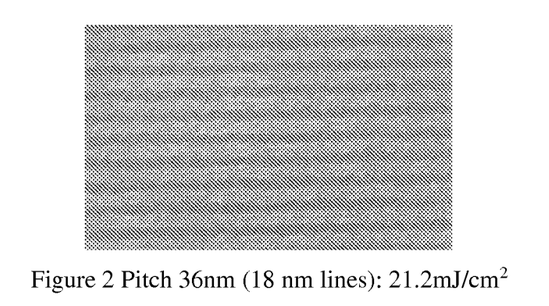
FIG. 2: shows an SEM showing the resolution obtained from example 2.

Example 1 was repeated but 150 mL of PGME was used to reduce the solids content. The resulting film thickness was 18 nm and the exposure was 21.2 mJ/cm$^2$. FIG. 2 shows the resulting 18 nm lines and spaces for example 2.

Composition Example 3

Example 1 was repeated using fullerene II in place of fullerene I. A 48 mJ/cm$^2$ exposure dosage was used. FIG. 3 shows the resulting 25 nm lines and spaces for example 3.

Composition Example 4

Figure 4:
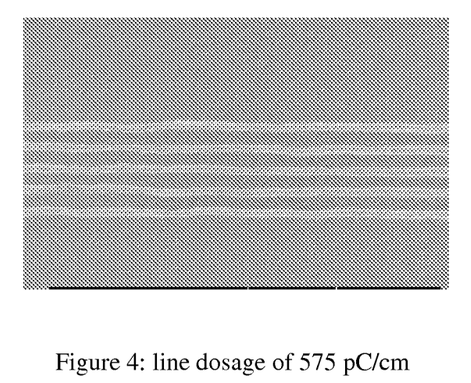
FIG. 4: shows an SEM showing the resolution obtained from example 4.

Example 1 was repeated using an E-beam exposure in place of 13-14 nm exposure. Area dose testing established a sensitivity of 90 μC/cm2 at 30 keV. For high resolution patterning a line dose of 575 pC/cm was applied at a nominal half-pitch of 50 nm, given lines of ~20 nm with ~30 nm spaces. FIG. 4 shows the resulting lines and spaces for example 4.

Composition Example 5

Figure 5:
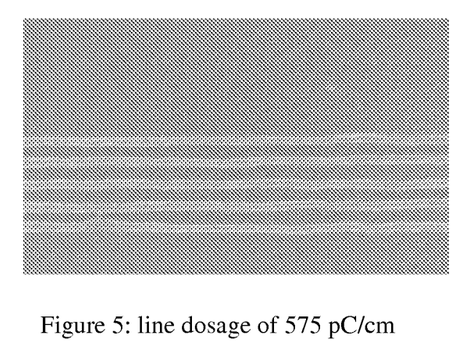
FIG. 5: shows an SEM showing the resolution obtained from example 5.

Example 3 was repeated using an E-beam exposure of 90 μC/cm$^2$ at 30 keV in place of 13-14 nm exposure. For high resolution patterning a line dose of 575 pC/cm was applied at a nominal half-pitch of 50 nm, given lines of ~20 nm with ~30 nm spaces FIG. 5 shows the resulting lines and spaces for the example 5.

Composition Example 6

Figure 6:
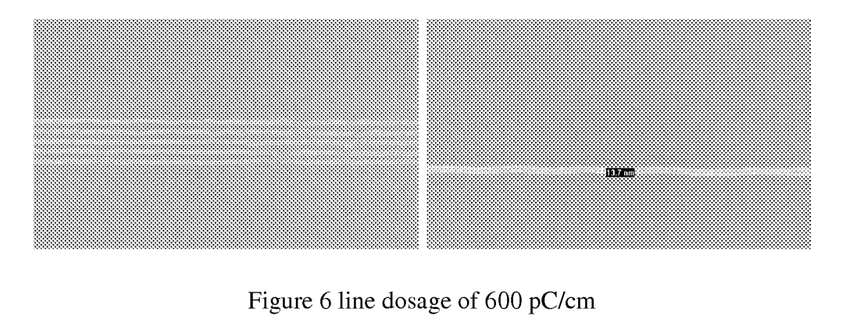
FIG. 6: shows an SEM showing the resolution obtained from example 6.

The formulation of Example 1 was repeated using 0.125 g of fullerene I and 0.125 g of a fullerene having tetraethylene glycol esters capped with acetic acid to provide acetate esters. The composition was applied to a silicon wafer and spin coated at 500 rpm for 5 sec followed by 2000 rpm for 60 sec. The coated wafer was then heated on a hot plate at 75° C. for 5 min to give a film of approximately 25 nm. The wafer was imagewise exposed to 40 μC/cm² of E-beam radiation and post exposure baked at 90° C. for 3 min. For high resolution patterning a line dose of 600 pC/cm was applied at a nominal half-pitch of 50 nm, given lines of ~20 nm with ~30 nm spaces The unexposed areas were removed by puddle development in a 50:50 blend of monochlorobenzene and isopropyl alcohol for 20 sec followed by an isopropyl alcohol rinse. FIG. 6 shows the resulting lines and spaces for example 6.

The invention claimed is:

1. A photoresist composition comprising at least one fullerene compound comprising the general formula:

a wherein Z forms a ring structure with the C2x fullerene chosen from A, B, and C below:

A

B

C wherein x is at least 10, y is 1-6, $R_1$ is a $C_1$ to $C_{30}$ branched or unbranched, substituted or unsubstituted alkyl, cycloalkyl, aryl, aralkyl, heterocyclic, alkylheterocyclic substituent or a substituent which coordinates with a least one metal, and $R_2$ is a substituent which coordinates with at least one metal, and wherein $R_3$, $R_4$ and $R_5$ is, each independently, a 1-6, $R_1$ is a $C_1$ to $C_{30}$ branched or unbranched, substituted or unsubstituted alkyl, cycloalkyl, aryl, aralkyl, heterocyclic, alkylheterocyclic substituent or a substituent which coordinates with a least one metal, b. at least one solvent,
c. at least one photoacid generator, and
d. optionally, at least one of a component chosen from a crosslinker, an alkali soluble and polymer protected by an acid-labile group.

2. The composition of claim 1, wherein the acid-labile group comprises an alkoxycarbonyl group.

3. The composition of claim 1, wherein, when y >2, at least one of the R1, R3, R4 and/or R5 substituents is a —COO-alkyl-aryl-(CH2)n-O—$R_o$ substituent, wherein alkyl is a branched or unbranched, substituted or unsubstituted divalent alkyl chain of 1-16carbons with or without one or more heteroatoms substituted into the chain, aryl is a substituted or unsubstituted divalent phenyl group, heteroaromatic group, or fused aromatic or fused heteroaromatic group, and $R_o$ is H or an acid labile group.

4. The composition of claim 3, wherein the metal is comprised of non-fullerene bonded ligands.

5. The composition of claim 3, wherein the heteroatoms are one or more of oxygen, nitrogen, sulfur, or oxides of sulfur.

6. The composition of claim 1, wherein the metal is chosen from a transition metal, alkali metal, alkaline earth metal, a lanthanide metal, an actinide metal, metalloids, metals from groups 13, 14 and 15 of the periodic table and their respective cations.

7. The composition of claim 1, further comprising at least one fullerene comprising the general formula:

wherein x is at least 10, y is 1-6, n is 0 -1, alkyl is a branched or unbranched, substituted or unsubstituted divalent alkyl chain of 1-16carbons with or without one or more heteroatoms substituted into the chain, aryl is a substituted or unsubstituted divalent phenyl group, heteroaromatic group, or fused aromatic or fused heteroaromatic group, and R is the same or different and is H or an acid labile group.

8. The composition of claim 1, wherein the substituent which coordinates with at least one metal is a monodentate or a polydentate ligand.

9. The composition of claim 8, wherein the substituent which coordinates with at least one metal is at least one of a bipyridyl, a crown ether, an ethylene diamine monomer or oligomer, a porphyrines, an ethylene diamine tetraacrylate, a peptide, a polysaccharide, phosphine, phosphates, carboxylates, and/or ethylene oxide monomers or oligomers, cyclic polyamides and heterocycles.

10. The composition of claim 1, further comprising at least one fullerene comprising the general formula:

$C_{2x}(>C-(COO-(CH_2CH_2-O)_a-R)_2)_y$ wherein x is at least 10, y is 1-6, a is 1-10 and R is H or an acid labile group and wherein the —CH₂CH₂—O— may be optionally substituted with fluorine atoms.

11. The composition of claim 1, wherein the at least one photoacid generator comprises an onium salt compound, a triphenylsulphonium salt compound, a sulfone imide compound, a halogen-containing compound, a sulfone compound, a sulfonate ester compound, a quinone-diazide compound, a diazomethane compound, an iodonium salt compound, an oxime sulfonate compound or a dicarboxylimide sulfonate compound.

12. A fullerene comprising the general formula:

wherein Z forms a ring structure with the C2x fullerene chosen from A, B, and C below:

A wherein x is at least 10, y is 1-6, $R_1$ is a $C_1$ to $C_{30}$ branched or unbranched, substituted or unsubstituted alkyl, cycloalkyl, aryl, aralkyl, heterocyclic, alkylheterocyclic substituent or a substituent which coordinates with a least one metal, and $R_2$ is a substituent which coordinates with at least one metal, and wherein $R_3$, $R_4$ and $R_5$ is, each independently, a 1-6, $R_1$ is a $C_1$ to $C_{30}$ branched or unbranched, substituted or unsubstituted alkyl, cycloalkyl, aryl, aralkyl, heterocyclic, alkylheterocyclic substituent or a substituent which coordinates with a least one metal, and wherein fullerene C is a nonmethanoyl fullerene.

13. The fullerenes of claim 12, wherein, when y>2, at least one of the R1, R3, R4 and/or R5 substituents is a —COO-alkyl-aryl-(CH2)n-O—$R_o$ substituent, wherein alkyl is a branched or unbranched, substituted or unsubstituted divalent alkyl chain of 1- 16 carbons with or without one or more heteroatoms substituted into the chain, aryl is a substituted or unsubstituted divalent phenyl group, heteroaromatic group, or fused aromatic or fused heteroaromatic group, and $R_o$ is H or an acid labile group.

14. The fullerenes of claim 13, wherein the heteroatoms are one or more of oxygen, nitrogen, sulfur, or oxides of sulfur.

15. The fullerenes of claim 13, wherein the acid labile group comprises an alkoxycarbonyl group.

16. The fullerenes of claim 12, wherein the metal is chosen from a transition metal, alkali metal, alkaline earth metal, a lanthanide metal, an actinide metal, metalloids, metals from groups 13, 14 and 15 of the periodic table and their respective cations.

17. The fullerenes of claim 16, wherein the metal is comprised of non-fullerene bonded ligands.

18. The composition of claim 12, wherein the substituent which coordinates with at least one metal is a monodentate or a polydentate ligand.

19. The composition of claim 18, wherein the substituent which coordinates with at least one metal is at least one of a bipyridyl, a crown ether, an ethylene diamine monomer or oligomer, a porphyrines, an ethylene diamine tetraacrylate, a peptide, a polysaccharide, phosphine, phosphates, carboxylates, and/or ethylene oxide monomers or oligomers, cyclic polyamides and heterocycles.

* * * * *